United States Patent
Park

(10) Patent No.: US 11,992,384 B2
(45) Date of Patent: May 28, 2024

(54) HEADGEAR FOR FIXING MOUTHPIECE

(71) Applicant: Mi Ra Park, Seoul (KR)

(72) Inventor: Mi Ra Park, Seoul (KR)

(*) Notice: Subject to any disclaimer, the term of this patent is extended or adjusted under 35 U.S.C. 154(b) by 1070 days.

(21) Appl. No.: 16/759,024

(22) PCT Filed: Oct. 29, 2018

(86) PCT No.: PCT/KR2018/012885
§ 371 (c)(1),
(2) Date: Apr. 24, 2020

(87) PCT Pub. No.: WO2019/088607
PCT Pub. Date: May 9, 2019

(65) Prior Publication Data
US 2021/0045844 A1    Feb. 18, 2021

(30) Foreign Application Priority Data
Oct. 31, 2017 (KR) .................. 10-2017-0143837

(51) Int. Cl.
*A61C 7/06* (2006.01)
*A61C 7/08* (2006.01)
(Continued)

(52) U.S. Cl.
CPC .................. *A61C 7/06* (2013.01); *A61C 7/08* (2013.01); *A61F 5/048* (2013.01); *A61F 5/05891* (2013.01); *A61F 7/12* (2013.01); *A61H 23/0236* (2013.01); *A61M 16/0009* (2014.02); *A61M 16/0066* (2013.01); *A61N 5/0624* (2013.01);
(Continued)

(58) Field of Classification Search
CPC .................................. A61C 7/06; A61C 7/065
See application file for complete search history.

(56) References Cited

U.S. PATENT DOCUMENTS 4,375,355 A * 3/1983 Dahan .................... A61C 7/065
                                                             433/5
4,453,917 A * 6/1984 Nodai ...................... A61C 7/06
                                                             433/5
(Continued)

FOREIGN PATENT DOCUMENTS

JP      2010-502376 A      1/2010
JP      2012-529299 A      11/2012
(Continued)

*Primary Examiner* — Ralph A Lewis
(74) *Attorney, Agent, or Firm* — NKL LAW; Jae Youn Kim

(57) ABSTRACT

A headgear can be worn on a user's head to adjustably fix a mouthpiece inserted in an oral cavity. The headgear includes: a front pad brought into contact with and pressed against a front pressure point of an outer surface of the buccinator between the zygomatic bone and the mandible in the face region; one or more rear pads brought into contact with and pressed against one or more rear pressure points so that a resultant force becomes a reaction force paired with a pressing force of the front pad, in a region from the top to the back of the head; a frame fixing the front pad and the rear pads; a front horizontal bar fixed to the frame at a position in front of the lip region of the head; and an adjustment part installed on the front horizontal bar to mount the mouthpiece.

6 Claims, 11 Drawing Sheets

(51) Int. Cl.
- *A61F 5/048* (2006.01)
- *A61F 5/058* (2006.01)
- *A61F 7/12* (2006.01)
- *A61H 23/02* (2006.01)
- *A61M 16/00* (2006.01)
- *A61N 5/06* (2006.01)
- *A61B 5/00* (2006.01)
- *A61B 5/01* (2006.01)
- *A61B 5/0531* (2021.01)
- *A61B 17/62* (2006.01)
- *A61B 17/64* (2006.01)
- *A61N 1/36* (2006.01)

(52) U.S. Cl.
CPC ............ *A61B 5/0002* (2013.01); *A61B 5/01* (2013.01); *A61B 5/0531* (2013.01); *A61B 5/6803* (2013.01); *A61B 17/62* (2013.01); *A61B 17/6433* (2013.01); *A61B 2562/029* (2013.01); *A61C 2204/002* (2013.01); *A61N 1/36* (2013.01); *A61N 2005/066* (2013.01); *A61N 2005/0661* (2013.01); *A61N 2005/0662* (2013.01)

(56) References Cited

U.S. PATENT DOCUMENTS

| | | | | |
|---|---|---|---|---|
| 4,988,291 A | * | 1/1991 | Grummons | A61C 7/06 433/5 |
| 5,158,451 A | * | 10/1992 | Pourcho | A61C 7/06 433/5 |
| 7,677,886 B2 | * | 3/2010 | Mitani | A61C 7/10 433/7 |
| 8,529,252 B2 | * | 9/2013 | Bukhary | A61C 7/065 433/5 |
| 2010/0190126 A1 | * | 7/2010 | Park | A61C 7/06 433/5 |

FOREIGN PATENT DOCUMENTS

| | | |
|---|---|---|
| JP | 2016-509513 A | 3/2016 |
| JP | 2017-524504 A | 8/2017 |
| KR | 10-2009-0018292 A | 2/2009 |
| KR | 10-0902533 B1 | 6/2009 |
| KR | 10-2012-0047227 A | 5/2012 |
| KR | 10-1295611 B1 | 8/2013 |
| KR | 10-1470992 B1 | 12/2014 |
| KR | 10-1680150 B1 | 11/2016 |
| WO | 2010-132399 A1 | 11/2010 |
| WO | 2014-097374 A1 | 6/2014 |

\* cited by examiner

HEADGEAR FOR FIXING MOUTHPIECE

TECHNICAL FIELD

The present invention relates generally to headgear for fixing a mouthpiece and, more particularly, to headgear that is worn on a user's head to fix a mouthpiece installed in an oral cavity and adjust the position and posture thereof.

BACKGROUND ART

In general, a maxillofacial orthodontic appliance used for the purpose of resolving orthodontic irregularities is known. In a conventional art, there are disclosed a head-side fixing structure (headgear) comprised of a vertical structure from the crown of the head to the tip of the chin and a horizontal structure from the forehead to the back of the head, a towed device installed at the vertical structure, and a maxillary expander installed at the towed device (mouthpiece).

Furthermore, a pronunciation and speech correction mechanism for improving English pronunciation is known. In another conventional art, there are disclosed a head mount (headgear) for head, and a connecting support, wherein an expansion plate in the oral cavity and a lip support (mouthpiece) at the edge of the mouth are connected to the head mount by the connecting support.

Furthermore, a face mask of a conventional art, illustrated in FIG. 11, has a structure in which a fixing wire of a pad that is fixed to the cheeks extends upward from below the mandible, and a frame is provided below the mandible.

In such orthodontic appliances, the headgear serve to achieve a purpose of pressing and shaping the skull by means of a pressing force even by wearing itself. For example, the headgear of a conventional art may press a specific portion of the skull by the head-side fixing structure comprised of the vertical structure from the crown of the head to the tip of the chin and the horizontal structure from the forehead to the back of the head. However, in a conventional art, since a description that the head itself is a subject of correction beyond correction of the shape of the oral cavity cannot be found, it is not necessarily intended to shape the skull.

On the other hand, the headgear is adapted to change the relative position of the mouthpiece with respect to the headgear or apply a force (tension) to the mouthpiece with respect to the headgear. For example, in a conventional art, the headgear tows the towed device forward, thereby enabling maxillary expansion of the mouthpiece. This improves the symptoms of lantern jaw, buck teeth, and the like. For example, in another conventional art, the headgear tows the connecting support so that the connecting support is opened in both left and right directions, enabling the mouthpiece to keep the lips in a horizontally wide shape.

DISCLOSURE

Technical Problem

However, headgear needs to be properly fixed to the user's head and maintained. If the headgear is not properly fixed to the head and maintained, a pressing force applied by the headgear itself will be applied to a wrong region. Furthermore, if the headgear is not properly fixed to the head and maintained, the relative position of a mouthpiece with respect to the headgear will change, and thus the direction of a force applied by the mouthpiece will be a wrong direction, and the magnitude of the force will be a different value from what is originally set. Moreover, if the headgear is not properly fixed to the head and maintained, the soft tissue of the user will be damaged every time the headgear moves, and thus a contact region with the headgear will be stimulated to cause a wound, or side effects of hair damage or loss. Therefore, it is important to fix and maintain the headgear. The headgear of a conventional art is difficult to change the relative position of the mouthpiece with respect to the headgear or to change a force applied to the mouthpiece.

However, if fixing of the headgear to the head is excessive, this causes inconvenience to the user. Since the headgear of a conventional art is provided with the vertical structure from the crown of the head to the tip of the chin, this causes a heat rash on the tip of the chin and the crown, and also causes difficulty in opening the mouth and severe pain. Additionally, since the horizontal structure from the forehead to the back of the head is provided, this causes a heat rash on the forehead and the scalp, and also causes inconvenience in wearing glasses.

The headgear is preferred as there are fewer restrictions on the movement of the user. In the headgear (face mask) of a conventional art, due to a structure in which the fixing wire of the pad that is fixed to the cheeks extends upward from below the mandible, this causes pain in the mandible of a patient, and due to a structure in which the frame is provided below the mandible, the uvula is compressed when the head is bowed, causing restriction in the user's movement.

It is necessary to improve fit of the headgear to the skull by making the headgear custom-made on the basis of the shape of the user's skull. This is because the shape of the skull is different for each user, and the asymmetry of the skull leads to an asymmetry of the face, mouth, and even body posture. The headgears of conventional arts are ready-made products made in S, M, and L sizes by determining their approximate sizes, and thus, are concepts that require various users to fit these ready-made devices. Therefore, there is a limit to the effect of correcting in response to the asymmetry of the head of the user. Additionally, in order to ensure that headgear is properly fixed, but to prevent excessive fixation, it is necessary to customize the headgear according to the shape of the skull.

Moreover, not only the headgear, but also the shape and position of a mouthpiece, a front pressure point, a front pad, a rear pressure point, a rear pad, a front frame, a rear frame, a front horizontal bar, and an adjustment part are all preferably custom-made to the shape of the user's skull. It is preferable that the headgear has an effect of correcting the shape of an asymmetric skull.

The headgear of a conventional art only attaches importance to connection with the mouthpiece in the oral cavity, and there is no intention to consider the magnitude and direction of a force applied to the mouthpiece and a force received from the mouthpiece, and no related configuration has been disclosed. For this reason, when the maxillary expander (mouthpiece) is used to expand the maxilla laterally or forward, unintended changes, such as asymmetry occur after maxillary expansion. With regard to the direction of force, the headgear of a conventional art does not cancel reaction that occur in a custom-made intraoral device applied to the maxilla. Therefore, only the action of the mouthpiece device in the oral cavity cannot be implemented as a result of correction.

Accordingly, the present invention has been made keeping in mind the above problems occurring in a conventional art, and an objective of the present invention is to provide headgear for fixing a mouthpiece, the headgear being capable of being properly fixed to the user's head and thus being maintained without a gap or movement.

Another objective of the present invention is to provide headgear for fixing a mouthpiece, the headgear allowing free movement of a jaw by avoiding excessive fixation to the head.

Still another objective of the present invention is to provide headgear for fixing a mouthpiece, wherein there is no restriction on the movement of a user.

Still another objective of the present invention is to provide headgear for fixing a mouthpiece, the headgear being custom-made on the basis of the shape of the user's skull, thereby improving fit for the skull, and maximizing the correction effect for an asymmetric skull.

Still another objective of the present invention is to provide headgear for fixing a mouthpiece, wherein not only the connection to the mouthpiece in the oral cavity, but also the direction of force of the mouthpiece are taken into consideration, so the reaction occurring in the mouthpiece is canceled and only the action of the mouthpiece device is implemented as a result, thereby making it possible to suppress the occurrence of unintended side effects.

Technical Solution

Headgear for fixing a mouthpiece according to the present invention for accomplishing the above objective is headgear which is worn on a user's head so as to adjustably fix the mouthpiece inserted in an oral cavity, and includes: one or more front pads brought into contact with and pressed against one or more predetermined front pressure points, in a face region of the head; one or more rear pads brought into contact with and pressed against one or more predetermined rear pressure points so that a resultant force becomes a reaction force paired with a pressing force of the front pads, in a region from top to back of the head; a front frame supporting the front pads so that a position and posture can be changed and fixed; a rear frame supporting the rear pads so that a position and posture can be changed and fixed; and an adjustment part disposed at a position in front of a lip region of the head to mount the mouthpiece, wherein the rear frame may be disposed above ear regions of the head, the front frame may be disposed in front of the ear region of the head, with one end thereof connected to the rear frame, and the other end thereof connected to the front pads, and the front pressure points may be specific portions of a maxilla on a face and are positions that do not limit functions of eyes, a nose, and a mouth.

Here, the front pressure points may be positions of an outer surface of a buccinator between a zygomatic bone and a mandible.

Furthermore, the front frame may be configured to extend forward downward from the rear frame to pass through depressed portions between the ear regions and the zygomatic bone of the head and extend to below the zygomatic bone.

Furthermore, in order to maximize an action force designed to be applied to the oral cavity by the mouthpiece, and to minimize a reaction force generated by the mouthpiece in response to the action force, the front and rear frames and the front and rear pads may be formed such that the reaction force may be transmitted to and canceled by at least one of the front and rear frames through the adjustment part.

The headgear may further include a front horizontal bar connected to the front frame or the rear frame and disposed in front of the lip region of the head, wherein the front horizontal bar may have an upper and lower double structure of an upper bar and a lower bar, and the adjustment part may be installed on a vertical rod installed between the upper and lower bars.

On the other hand, headgear for fixing a mouthpiece according to the present invention is headgear which is worn on a user's head so as to adjustably fix the mouthpiece inserted in an oral cavity, and includes: one or more front pads brought into contact with and pressed against one or more predetermined front pressure points, in a face region of the head; one or more rear pads brought into contact with and pressed against one or more predetermined rear pressure points so that a resultant force becomes a reaction force paired with a pressing force of the front pads, in a region from top to back of the head; a front frame supporting the front pads so that a position and posture can be changed and fixed; a rear frame supporting the rear pads so that a position and posture can be changed and fixed; and an adjustment part disposed at a position in front of a lip region of the head to mount the mouthpiece, wherein a shape or position of at least one of the mouthpiece and the headgear may be personalized to the user so that paired forces are applied to a region necessary for symmetry formation of the head on the basis of a measured shape of the head of the user.

Here, at least one of the mouthpiece and the headgear may be formed by 3D printing on the basis of measured shape data.

On the other hand, headgear for fixing a mouthpiece according to the present invention is headgear which is worn on a user's head so as to adjustably fix the mouthpiece inserted in an oral cavity, and includes: one or more front pads brought into contact with and pressed against one or more predetermined front pressure points, in a face region of the head; one or more rear pads brought into contact with and pressed against one or more predetermined rear pressure points so that a resultant force becomes a reaction force paired with a pressing force of the front pads, in a region from top to back of the head; a front frame supporting the front pads so that a position and posture can be changed and fixed; a rear frame supporting the rear pads so that a position and posture can be changed and fixed; an adjustment part disposed at a position in front of a lip region of the head to mount the mouthpiece; a power source provided in at least one of the mouthpiece and the headgear; and one or more function units connected to the power source to output a specific function, wherein the function units may include at least one of (1) a light emitter that emits infrared, visible, or ultraviolet light, (2) a sound device that produces sounds, (3) a low-frequency electric signal that applies an electric signal to a muscle or skin, (4) a vibrator that outputs physical vibration, (5) a cooler or warmer that changes and controls temperature, and (6) a blower or aspirator that changes and controls ventilation.

On the other hand, headgear for fixing a mouthpiece according to the present invention is headgear which is worn on a user's head so as to adjustably fix the mouthpiece inserted in an oral cavity, and includes: one or more front pads brought into contact with and pressed against one or more predetermined front pressure points, in a face region of the head; one or more rear pads brought into contact with and pressed against one or more predetermined rear pressure points so that a resultant force becomes a reaction force paired with a pressing force of the front pads, in a region from top to back of the head; a front frame supporting the front pads so that a position and posture can be changed and fixed; a rear frame supporting the rear pads so that a position and posture can be changed and fixed; an adjustment part disposed at a position in front of a lip region of the head to mount the mouthpiece; a power source installed in the mouthpiece, and comprised of a generator generating electrical energy by relative motion between a maxilla and mandible, and a power storage means storing the generated electrical energy; and one or more function units connected to the power source to output a specific function, wherein the function units may include at least one of (1) a light emitter that emits infrared, visible, or ultraviolet light, (2) a sound device that produces sounds, (3) a low-frequency electric signal that applies an electric signal to a muscle or skin, (4) a vibrator that outputs physical vibration, (5) a cooler or warmer that changes and controls temperature, and (6) a blower or aspirator that changes and controls ventilation.

Here, at least one of the mouthpiece and the headgear may include one or more sensor units provided to be connected to the power source, and a control unit controlling the function units to be operated by comparing a detection value detected by the sensor units with a predetermined reference value, wherein the sensor units may include at least one of (1) a temperature sensor, (2) a humidity sensor, (3) a skin resistance sensor, (4) a tension sensor, and (5) a distance sensor.

Here, at least one of the mouthpiece and the headgear may further include a communication unit provided, and the control unit may be configured to transmit the detection value detected by the sensor units to a predetermined terminal wirelessly through the communication unit.

Furthermore, the control unit may be configured to control operation of at least one of the function units in response to a command from the terminal through the communication unit.

Advantageous Effects

According to the present invention, there is provided headgear for fixing a mouthpiece, the headgear being capable of being properly fixed to the user's head and thus being maintained without a gap or movement.

There is further provided headgear for fixing a mouthpiece, the headgear allowing free movement of a jaw by avoiding excessive fixation to the head.

There is further provided headgear for fixing a mouthpiece, wherein there is no restriction on the movement of the user, thereby causing no interference with a frame when the head is bowed.

There is further provided headgear for fixing a mouthpiece, the headgear being custom-made on the basis of the shape of the user's skull, thereby improving fit for the skull, and maximizing the correction effect for an asymmetric skull.

Furthermore, not only the connection to the mouthpiece in the oral cavity, but also the direction of force of the mouthpiece are taken into consideration, so when the maxilla is expanded laterally or forward by a maxillary expander, reaction occurring in the mouthpiece is canceled and only the action of the mouthpiece device is implemented as a result. For example, there is provided headgear for fixing a mouthpiece, wherein in a device aimed to expand the maxilla forward, a force that cancels the reaction that the posterior teeth region is moved rearward may be applied to the headgear, thereby obtaining only an effect of expanding the maxilla forward, and in a device aimed to expand the maxilla forward and rearward, a force that cancels the reaction that the center of the maxilla collapses downward may be applied to the headgear, thereby obtaining an effect of expanding only the palate bone while maintaining the shape of the palate bone. Additionally, it is possible to suppress the occurrence of unintended changes, such as asymmetry after maxillary expansion.

DESCRIPTION OF THE REFERENCE NUMERALS IN THE DRAWINGS

Figure 1:
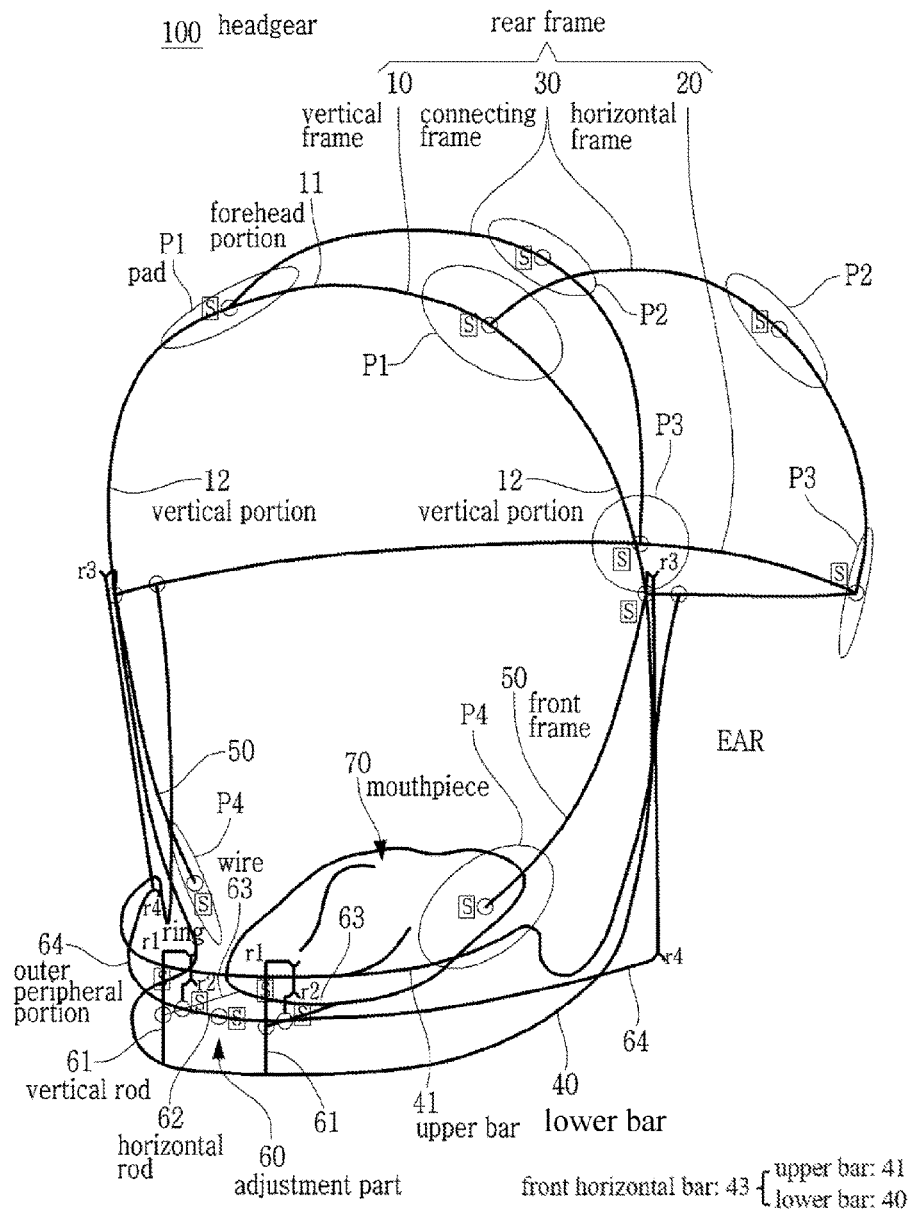
FIG. 1 is a front left side view illustrating headgear for fixing a mouthpiece according to an embodiment of the present invention.
Figure 2:
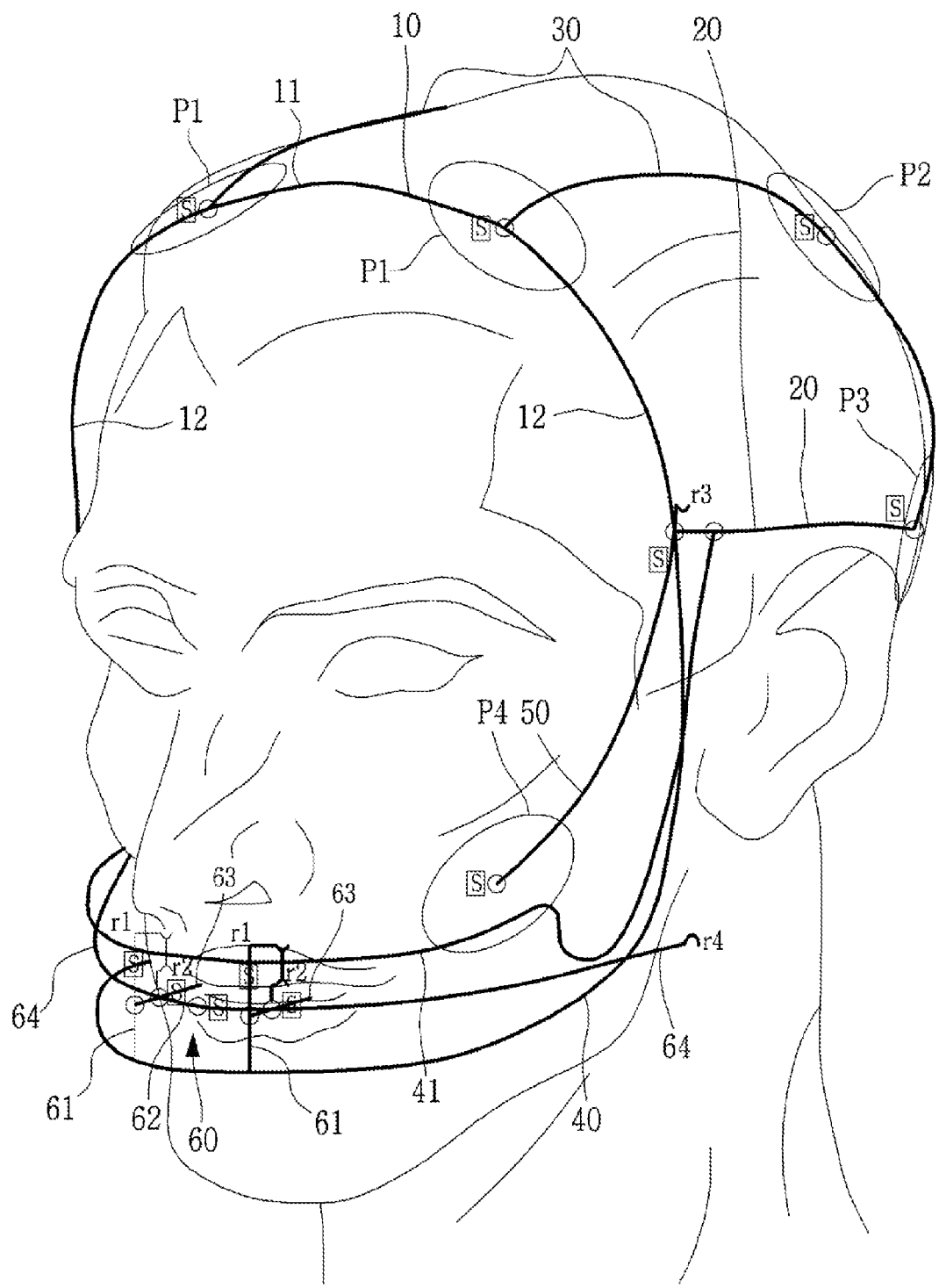
FIG. 2 is a front left side view illustrating a state in which a user wears the headgear for fixing the mouthpiece of FIG. 1.
Figure 3:
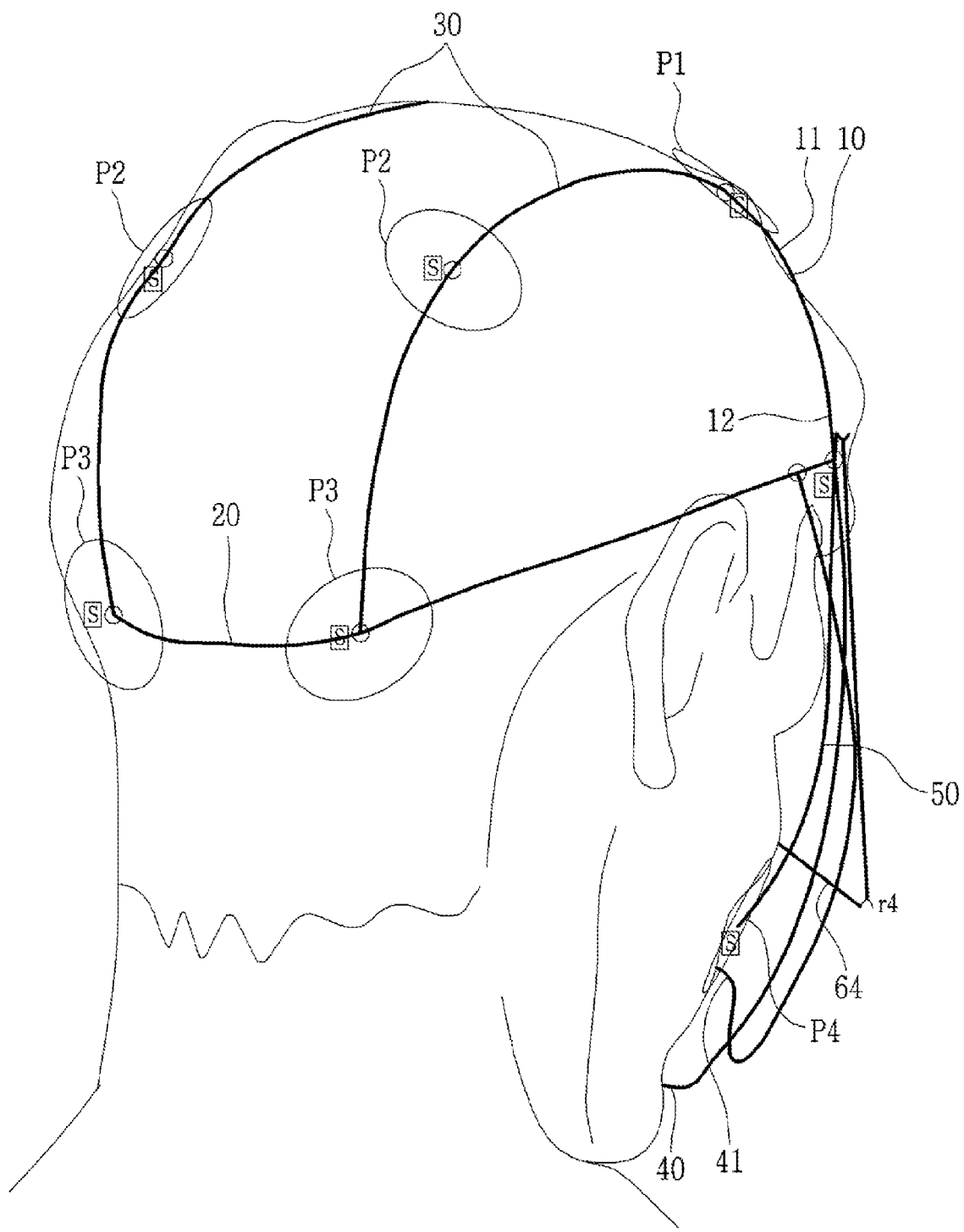
FIG. 3 is a rear right side view illustrating a state in which the user wears the headgear for fixing the mouthpiece of FIG. 1.
Figure 4:
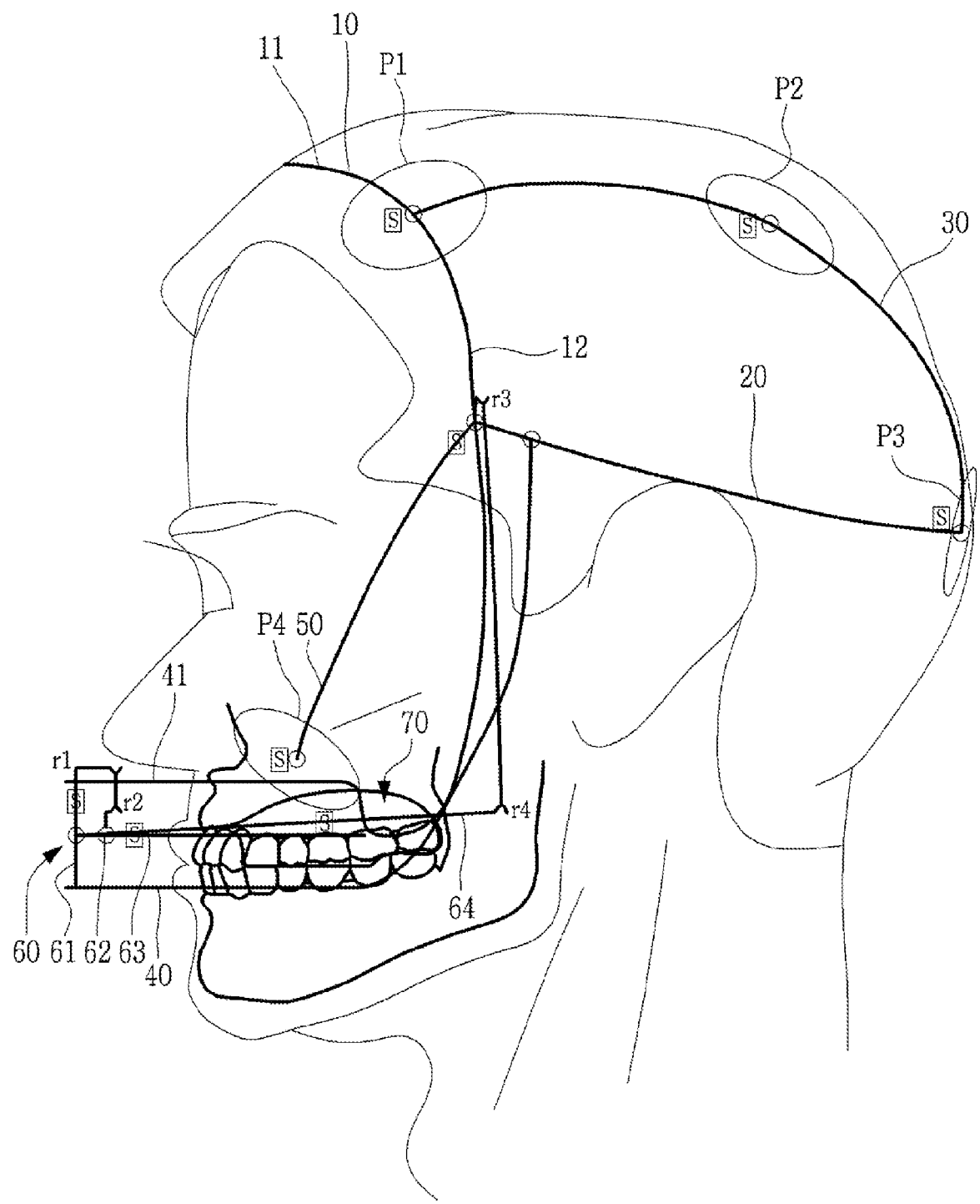
FIG. 4 is a left side view illustrating a state in which the user wears the headgear for fixing the mouthpiece of FIG. 1.
Figure 5:
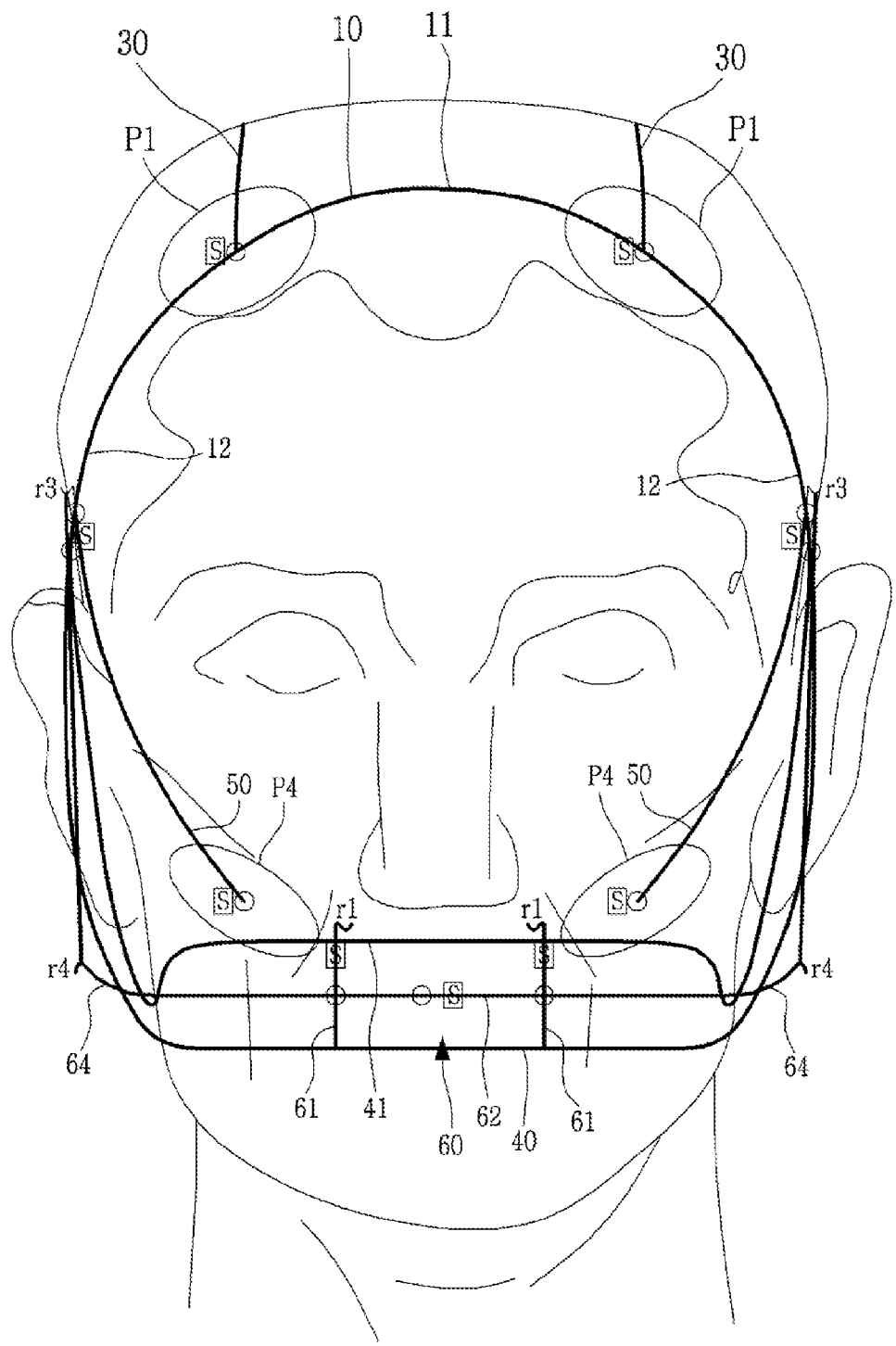
FIG. 5 is a front view illustrating a state in which the user wears the headgear for fixing the mouthpiece of FIG. 1.

10: vertical frame
20: horizontal frame
30: connecting frame
43: front horizontal bar
50: front frame
60: adjustment part
70: mouthpiece
100: headgear

BEST MODE

Hereinafter, exemplary embodiments of the present invention will be described in detail with reference to the accompanying drawings. Advantages and features of the present invention, and a method of achieving the same will be more clearly understood from the following embodiments when taken in conjunction with the accompanying drawings. However, various changes to the following embodiments are possible and the scope of the present invention is not limited to the following embodiments. The present embodiments are presented to make complete disclosure of the present invention and help those who are ordinarily skilled in the art best understand the invention, and the present invention should be defined by the appended claims. Throughout the drawings, the same reference numerals will refer to the same or like parts.

Unless otherwise defined, all terms (including technical and scientific terms) used herein have the same meaning as commonly understood by one of ordinary skill in the art to which the present invention belongs. It will be further understood that terms used herein should be interpreted as having a meaning that is consistent with their meaning in the context of this specification and the relevant art and will not be interpreted in an idealized or overly formal sense unless expressly so defined herein.

It will be understood that when an element is referred to as being "connected" to another element, it can be directly connected to the other element or intervening elements may be present therebetween. It will be understood that a module performing a certain function may be implemented together with some other modules, or multiple modules each having a function may be integrated and implemented as a single module. Additionally, some electronic functional blocks may be realized by the execution of software, or may be realized in a state in which the software is implemented in hardware through an electrical circuit.

<Overall Configuration>

As illustrated in FIGS. 2 to 5, headgear 100 for fixing a mouthpiece according to the present invention is headgear 100 which is worn on the user's head so as to adjustably fix a mouthpiece 70 inserted in the oral cavity. The headgear 100 is characterized by including one or more front pads P4, one or more rear pads P1 to P3, a front frame 50, rear frames 10, 20 and 30, and an adjustment part 60.

The front pads P4 are pads that are brought into contact with and pressed against at one or more front pressure points that are predetermined, in the face region of the head.

The front pressure points are specific portions of the maxilla on the face, and are positions that do not limit the functions of the eyes, nose, and mouth. The front pressure points may be depressed portions in a skeletal shape or muscle configuration. As a particularly preferred position among the depressed portions, an outer surface of the buccinator between the zygomatic bone (cheekbone) and the mandible may be selected. Alternatively, the position between the zygomatic bone and the nose, the position between the nose and the lips (philtrum), and the position between the philtrum and the zygomatic bone may also be selected as the depressed front pressure points. However, when the shape of the front pads P4 is a depressed shape or a donut shape, protruding portions such as the zygomatic bone, nose, and the like may be selected as the front pressure points.

It is preferable that the front pads P4 are provided as a pair of front pads provided on the left and right sides, respectively. However, when the front pads P4 are provided on only one side of the left or the right side, the positions of the rear pads P1 to P3 may be adjusted thereby fixing the headgear 100 and shaping the skull. The material of the pad should be made of a component that is harmless to the skin. However, the present invention is not limited thereto as long as a material capable of buffer skin irritation due to pressurization of a contact region, such as foamed resin or sponge.

It is an essential limitation in the present invention to limit the front pressure points to positions that do not limit the functions of the eyes, nose, and mouth while being specific portions of the maxilla on the face, and this is a characteristic configuration of the present invention, since it is not possible to find an example describing a technical configuration in which these points are selected as pressure points. For example, in a conventional art, headgear is fixed to the head so as to cover the tip of the chin and the forehead, which may cause problems in wearing glasses as well as opening the mouth. In the present invention, by selecting the outer surface of the buccinator between the zygomatic bone and the mandible as the front pressure point, strong and smooth fixation is possible in any position in front of the ear regions of the head even without the support point of the headgear 100. Therefore, it is possible to dramatically increase the freedom of the entire face region, from the chin to the forehead.

The rear pads P1 to P3 are pads that are brought into contact with and pressed against one or more rear pressure points. The rear pressure points are points which are predetermined such that a resultant force becomes a reaction force paired with a pressing force of the front pads P4 at the front pressure points, in a region from the top to the back of the head. Since the front pressure points are specific portions of the face, they correspond to front portions when viewed from the entire head and preferably correspond to lower front portions. Therefore, a virtual central point of the rear pressure points which can apply the reaction force becomes an upper rear portion of the head. On the basis of this upper rear portion, it is possible to set a plurality of distributed portions (e.g., positions of P1 to P3 illustrated) in which the resultant force becomes the reaction force. This distributed portions can be calculated geometrically simply from the point of view of symmetry, or can be ascertained by feeling by the user wearing the headgear 100. Furthermore, when it is necessary to press a portion protruding than a normal position of the shape of the head, the position of the protruding portion may be determined to be included in the plurality of distributed positions, and when it is necessary to push a depressed portion to a normal position, the position of the periphery of the depressed portion may be determined to be included in the plurality of distributed positions.

The front frame 50 is a frame that supports the front pads P4 so that a position and posture can be changed and fixed. The rear frames 10, 20, and 30 are frames that support the rear pads P1 to P3 so that a position and posture can be changed and fixed. In an illustrated example, the rear frames 10, 20, and 30 are comprised of a vertical frame 10, a horizontal frame 20, and a connecting frame 30. However, the front frame and the rear frames may be configured differently, and the number or arrangement direction thereof is not limited. For example, it should be understood that other configurations also belong to the present invention as long as they have a function to enable the position and posture change while fixing pads.

In an illustrated example, the vertical frame 10 is a substantially C-shaped frame with a lower side open, the direction of the plane (normal direction of the plane formed by the frame) is oriented toward the front-rear direction, and is comprised of a forehead portion 11, and a vertical portion 12. The horizontal frame 20 is a substantially C-shaped frame with a front side open, the direction of the plane is oriented toward the up-down direction, and an open end thereof is connected to a middle portion of the vertical frame 10. The connecting frame 30 is a frame that connects the vertical frame 10 and the horizontal frame 20 to each other. Therefore, the vertical frame 10 and the horizontal frame 20 form a boundary, so that the rear frames 10, 20, and 30 only exist in the rear region with respect to a vertical line in front of the ear region of the head, and only exist in an upper region with respect to a horizontal line above the ear regions. That is, the rear frames 10, 20, and 30 are disposed above the ear regions of the head, and the front frame 50 is disposed in front of the ear regions of the head, with one end thereof connected to the rear frames 10, 20, and 30, and the other end thereof connected to the front pads P4.

The front frame 50 is disposed in front of the ear regions of the head, with one end thereof connected to the rear frames 10, 20, and 30, and the other end thereof connected to the front pads P4. In an illustrated example, the front frame 50 is illustrated in a form of a wire frame arm that extends long downward from a mid-height portion of the vertical portion 12 of the vertical frame 10. However, the present invention is not limited thereto, and the front frame may be variously modified. For example, the front frame 50 may be realized in a form of an mid-length wire frame arm (not illustrated) that extends substantially horizontally forward from a lower height portion of the vertical portion 12 of the vertical frame 10, or in a form of a short arm (not illustrated) that extends upward and rearward from a front horizontal bar 43 which is connected to the front frame or the rear frame and disposed at a position in front of the lip region of the head. Therefore, by the front frame 50, with respect to the vertical line in front of the ear regions of the head, only the front frame 50 exists in the front region, while the rear frames 10, 20, and 30 do not exist.

That is, as illustrated in the drawings, it is preferable that the rear frames 10, 20, and 30 are disposed above the ear regions of the head, and the front frame 50 is disposed in front of the ear regions of the head. In an illustrated example, the vertical frame 10 is a front boundary of the ear regions, and the horizontal frame 20 is an upper boundary of the ear regions. As can be seen from the drawings, the ear regions are located behind the front boundary and below the upper boundary. Therefore, the outer ear region is free from being pressed and free from interfering with listening.

When the front pressure points are determined, the front pads P4 are disposed on the front frame 50 with a position and posture adjusted and a pressing force set, and when the central point of the rear pressure points and the distributed rear pressure points are determined, the rear pads P1 to P3 are disposed on the rear frames 10, 20, and 30 with a position and posture adjusted and a pressing force set.

As such, when the front pressure points and the rear pressure points of the head are determined, and the front pads P4 and rear pads P1 to P3 are disposed at these front pressure points and rear pressure points, and these front pads P4 and rear pads P1 to P3 are pressed by the front frame 50 and the rear frames 10, 20, and 30, protruding portions of the head existing at the front pressure points and the rear pressure points are pressed and pushed, thereby obtaining an effect of improved symmetry of the head.

The front horizontal bar 43 is a bar which is connected to the front frame 50 or the rear frames 10, 20, and 30 and is disposed at a position in front of the lip region of the head. In an illustrated example, the front horizontal bar 43 is a substantially C-shaped frame that extends forward and is smoothly connected to the vertical portion 12 of the vertical frame 10, has a rear side open, and the direction of the plane is oriented toward the up-down direction. The front horizontal bar 43 is a structure for installing the adjustment part 60.

The adjustment part 60 is a member which is disposed at a position in front of the lip region of the head to mount the mouthpiece. In an illustrated example, the adjustment part is installed on the front horizontal bar 43 to mount the mouthpiece 70 so as to be adjustable with respect to at least one of the front, rear, left, right, top, and bottom. For example, adjustment in the front-rear direction is to adjust a forward traction applied to the mouthpiece 70, adjustment in the left-right direction is to adjust the orientation of the horizontal direction of the mouthpiece 70 and adjust the variation in the width direction of a support point outside the oral cavity according to expansion in the width direction, and adjustment in the up-down direction is to adjust the condition in which the mouthpiece 70 is brought into close contact with the palate in the oral cavity. The mouthpiece 70 has a pair of wires 63 protruding forward, front ends of the wires 63 are connected to each other by a horizontal rod 62, and the horizontal rod 62 extends long to form an outer peripheral portion 64. Each of the horizontal rod 62 and the wire 63 is provided with a length adjustment mechanism by screw engagement of, for example, a female screw and a male screw. A sensor unit S (e.g., a distance sensor) for detecting a length or a change in the length, and a communication unit 23 for transmitting the detection amount of the sensor to an external terminal (not illustrated) may be provided.

The headgear 100 according to the present invention is not only kept closely in contact with the head, but also brings the effect of skull shaping as the headgear 100 itself. However, the present invention is not limited thereto. The headgear 100 is not only connected to the mouthpiece in the oral cavity, but also determines the position, size, and number of the front and rear pressure points in consideration of the direction of force of the mouthpiece. That is, for an action and reaction that occurs when the mouthpiece applies a force on the maxilla according to a specific purpose, the front pressure points and the rear pressure points of the headgear 100 are determined such that the headgear generates a force in the direction of validating the action and canceling the reaction.

According to this, when the maxilla is expanded laterally or forward by a maxillary expander, the reaction occurring in a custom-made intraoral mouthpiece device applied to the maxilla is canceled so that only the action of the intraoral mouthpiece device to the maxilla is realized as a result. For example, in a device aimed to expand the maxilla forward, a force that cancels the reaction that the posterior teeth region is moved rearward may be applied to the headgear, thereby obtaining only an effect of expanding the maxilla forward, and in a device aimed to expand the maxilla forward and rearward, a force that cancels the reaction that the center of the maxilla collapses downward may be applied to the headgear, thereby obtaining an effect of expanding only the palate bone while maintaining the shape of the palate bone. This makes it possible to suppress the occurrence of unintended changes, such as asymmetry after maxillary expansion.

Effects According to the Present Invention

According to the present invention, a front pressure point is determined, for example, at the position of the outer surface of the buccinator between the zygomatic bone and the mandible, i.e., approximately below the zygomatic bone, the position not limiting the functions of the eyes, nose, and mouth while being a specific portion of the maxilla on the face, and one or more rear pressure points that applies a reaction force paired with a force of the front pressure point are determined in the region from the top to the back of the head. For example, when four rear pressure points are determined, a resultant force thereof is gathered to one point, and a force of the one point becomes a reaction force paired with a resultant force of forces of front pressure points. Therefore, the headgear 100 is kept closely in contact with the head.

Additionally, since the front pressure point supported by force is only a specific portion of the maxilla on the face, such as near below the zygomatic bone, and exists only at a position that does not limit the functions of the eyes, nose, and mouth, the movements of the mandible, chin, and neck are not restrained. Therefore, the present invention imparts a very large freedom to the user (compared to a conventional art).

Moreover, in order to maximize an action force designed to be applied to the oral cavity by the mouthpiece, and to minimize a reaction force generated by the mouthpiece in response to the action force, it is preferable that the front and rear frames and the front and rear pads are formed such that the reaction force is transmitted to and canceled by at least one of the front and rear frames through the adjustment part.

According to this, the front and rear pressure points are determined such that the headgear 100 applies a force in a direction that maintains the action generated in response to a force applied by the mouthpiece in the oral cavity for a predetermined purpose and cancels the reaction, and thus, in the oral cavity, only the effect of the action occurs and the effect of the reaction disappears. This makes it possible to suppress the occurrence of unintended changes in the maxilla.

<Detailed Configuration Offrame>

It is preferable that the front frame 50 and the rear frames 10, 20, and 30 are formed, for example, in a wire form. Here, the wire refers to a member having a small volume, a shape extending in the longitudinal direction, and high rigidity. The material, thickness, and cross-sectional shape of the wire may vary depending on the user's age, skin condition, skeletal condition, required support force, or pressing force.

Constructing the frames with the wire makes it possible to maintain the shape suitable for the skull, thereby preventing separation of the rear pads and the front pads against the front and rear pressure points, providing close contact with the head, and maximizing ventilation of the scalp region (including the skin under the hair and the facial skin).

<Preferred Installation Position of Front Frame>

On the other hand, the front frame 50 may be configured to be connected to the rear frames 10, 20, and 30. However, when considering the skull and muscles of the face, there may be the most preferable installation position, and it is preferable that the front frame 50 is installed at that position, and this may provide an effect that the frame can be in close contact with the face.

To this end, it is preferable that the front frame 50 is configured to extend forward downward from the rear frames 10, 20, and 30 to pass through depressed portions between the ear regions and the zygomatic bone of the head and extend to below the zygomatic bone. That is, as in an illustrated example, it is preferable that the front frame 50 is formed in a form of a wire frame that extends long downward from the mid-height portion of the vertical portion 12 of the vertical frame 10.

When the front frame 50 is installed so as to extend forward downward as shown in the illustrated example, the front frame is disposed at the depressed portions between the ear regions and the zygomatic bone of the head and thus is brought into close contact with the face.

However, in a case where the close contact with the face is not considered to be important, various installation methods are possible. For example, the front frame 50 may be installed at a lower portion of the vertical portion 12 extending downward from the rear frames 10, 20, and 30. In this case, an installation length is shortened, and thus the rigidity is increased. Furthermore, the front frame 50 may be installed on the front horizontal bar 43. In this case, the installation length is further shortened and the rigidity is further increased.

<Installation Area of Adjustment Part>

The adjustment part 60 is a member which is disposed at a position in front of the lip region of the head to mount the mouthpiece 70 so as to be adjustable with respect to at least one of the front, rear, left, right, top, and bottom. Therefore, a plane perpendicular to the front-rear direction becomes a plane to be adjusted.

In an illustrated example, the front horizontal bar 43 has an upper and lower double structure of an upper bar 41 and a lower bar 40, and the adjustment part 60 is installed on a vertical rod 61 installed between the upper bar 41 and the lower bar 40. However, it is preferable that the vertical rod 61 is movable in position in the left-right direction.

In this structure, a ring r2 of each of the wires 63 extending forward from the mouthpiece 70 is towed vertically upward through an elastic member, for example, a rubber band, by each ring r1 of the upper bar 41, thereby being given an upward force (upward traction). By this upward force, a front portion of the mouthpiece 70 is firmly attached to the maxilla. The traction by the elastic member is measured by a sensor unit S, for example, a sensor such as a spring scale. A measured traction value is transmitted to a terminal (not illustrated) through the communication unit 23, stored, and processed for post-processing such as history management and artificial intelligence processing.

The wire 63 is detachably connected to the vertical rod 61 by a ratchet and is towed forward, thereby being given a forward traction by an elastic force of the ratchet. By this traction, the mouthpiece 70 acts a force on the maxilla and palate, causing deformation of the skull. The vertical rod 61 is provided with a scale or a plurality of grooves, so that the position in the height direction can be precisely set when the ratchet is fastened. The vertical rod 61 may be provided with a sensor unit S, for example, a distance sensor, instead of the scale or grooves, so that a height value may be measured. A measured height value is transmitted to a terminal (not illustrated) through the communication unit 23, stored, and processed to perform post-processing such as history management and artificial intelligence processing.

Figure 7:
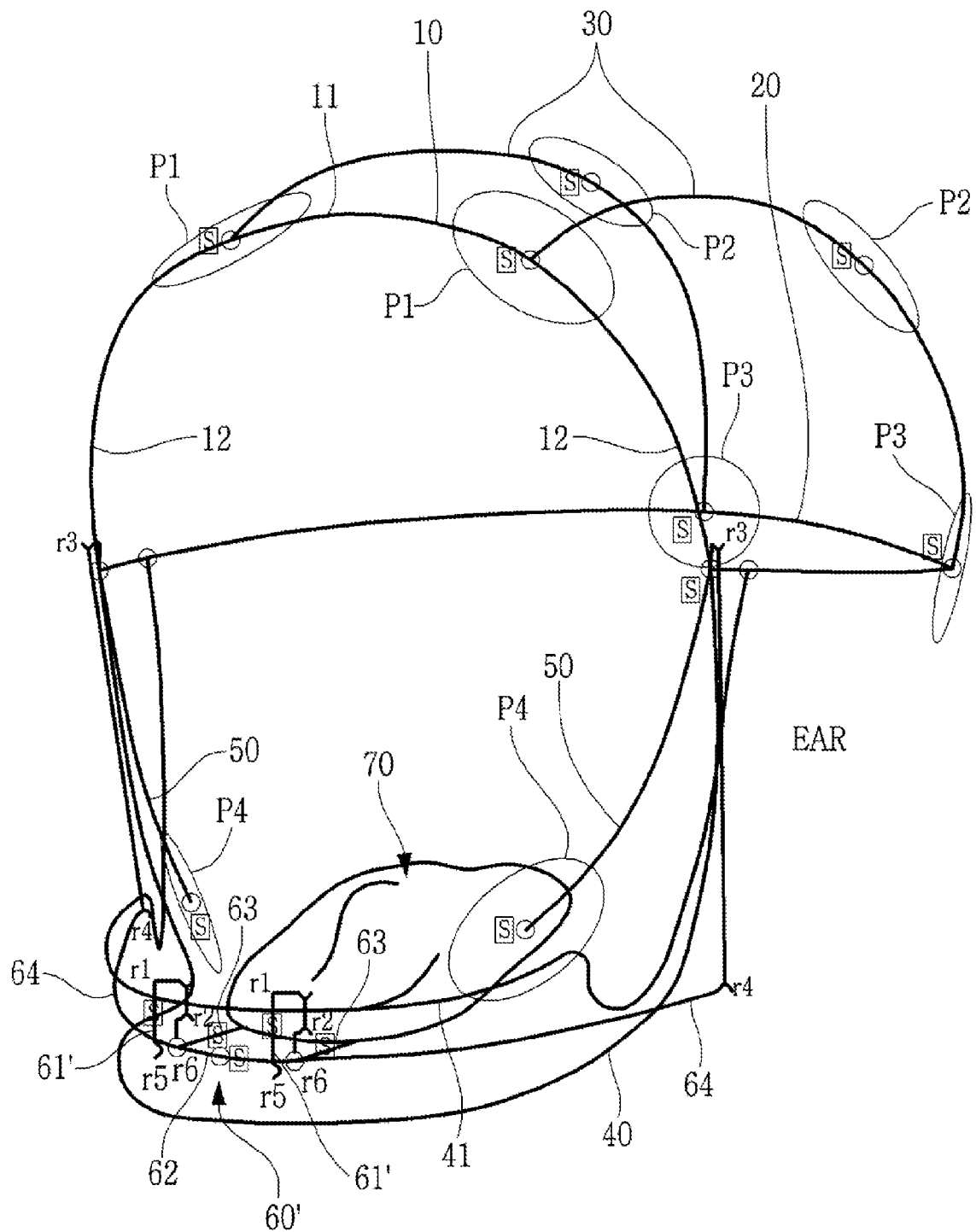
FIG. 7 is a front left side view illustrating headgear for fixing a mouthpiece according to another embodiment of the present invention.

However, in an adjustment part 60' according to another embodiment, as illustrated in FIG. 7, a member 61' having a ring r5 may be installed instead of the vertical rod 61, and a front ring r6 of each wire 63 may be towed horizontally forward through another elastic member, for example, a rubber band, by the ring r5, thereby being given a forward traction.

Figure 8:
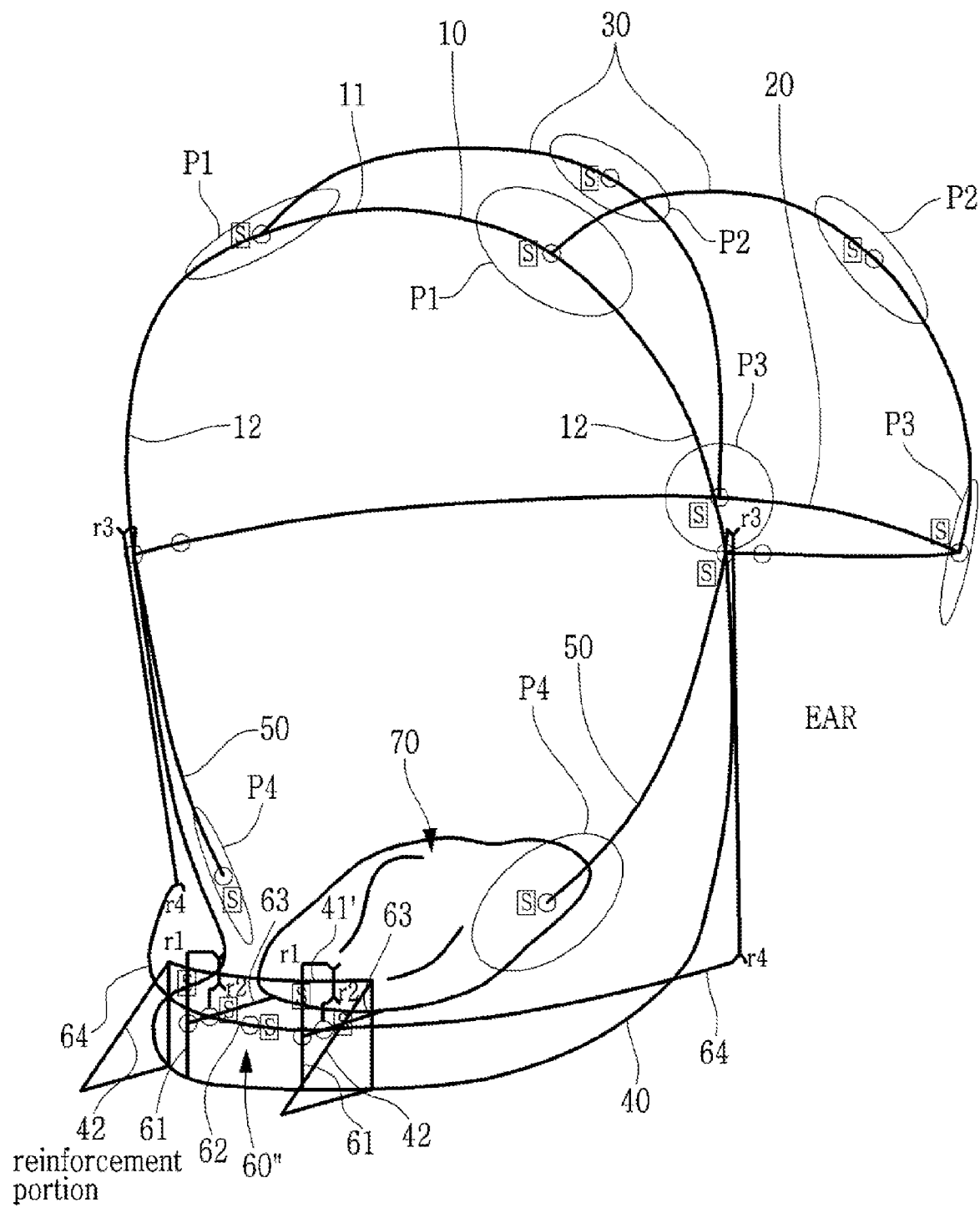
FIG. 8 is a front left side view illustrating headgear for fixing a mouthpiece according to still another embodiment of the present invention.
Figure 9:
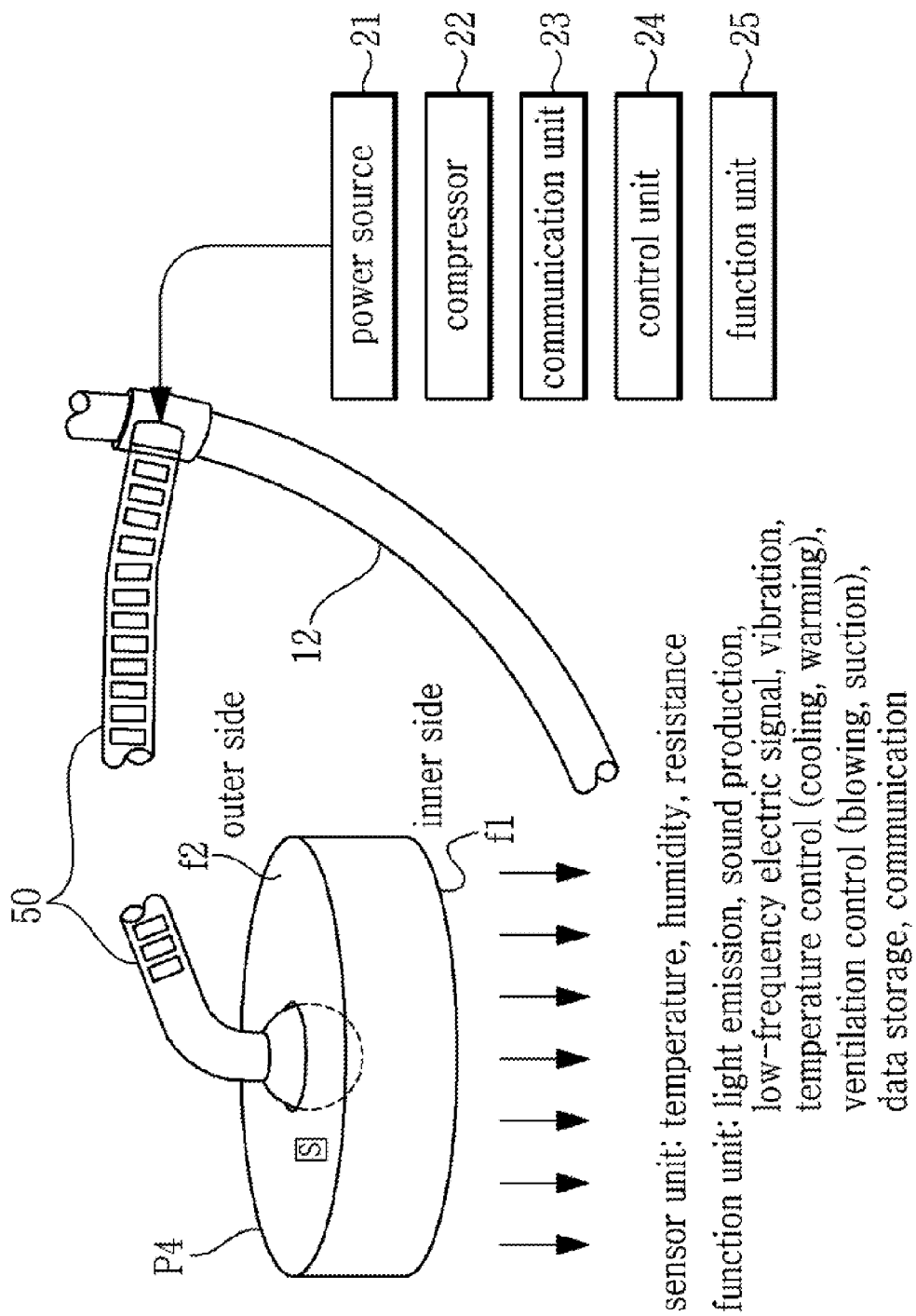
FIG. 9 is a perspective view illustrating the configuration and function of a pad and the connection structure to a frame.

Furthermore, in an adjustment part 60" according to still another embodiment, as illustrated in FIG. 8, the upper bar 41 may be formed short to form a shortened upper bar 41'. In this case, the shortened upper bar 41' may be fixed to the lower bar 40, and may be configured to have a reinforcement portion 42 to increase a supporting force.

In this structure, front portions of respective wires 63 are connected to each other by a horizontal rod 62, and the horizontal rod 62 is connected to an outer peripheral portion 64 extending from the front to each side and extending rearward. Rings r4 at the ends of the respective outer peripheral portions 64 are towed upward in the direction of rings r3 of the frames 10, 20, and 30, and 50 by another elastic member, for example, a rubber band.

Figure 6:
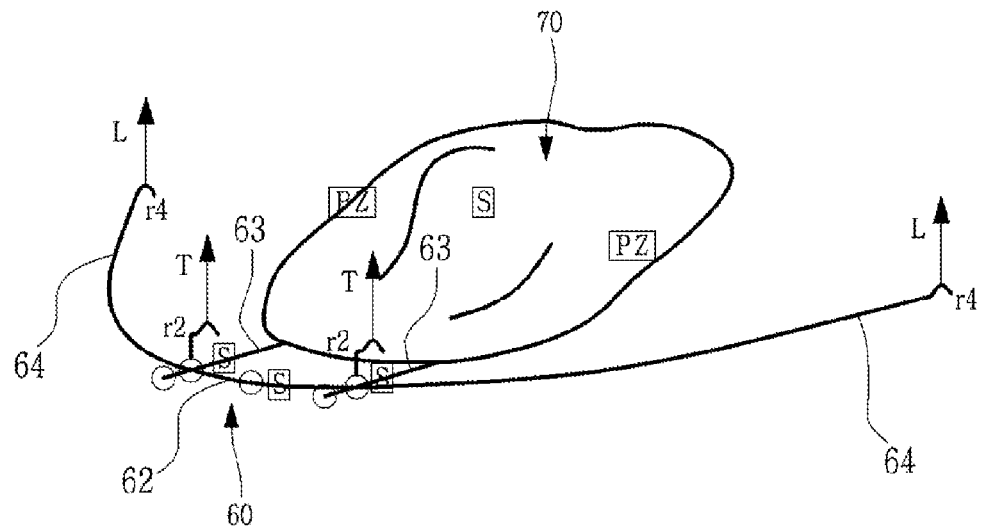
FIG. 6 is an explanatory view illustrating the operation of a horizontal rod and a wire mounted on a vertical rod of an adjustment part, and an outer peripheral portion.
Figure 6:
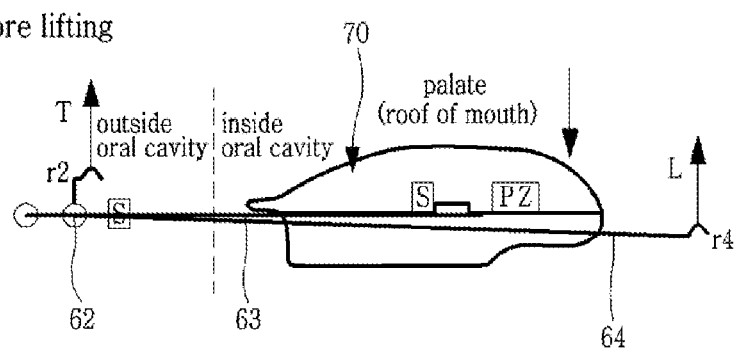
Figure 6:
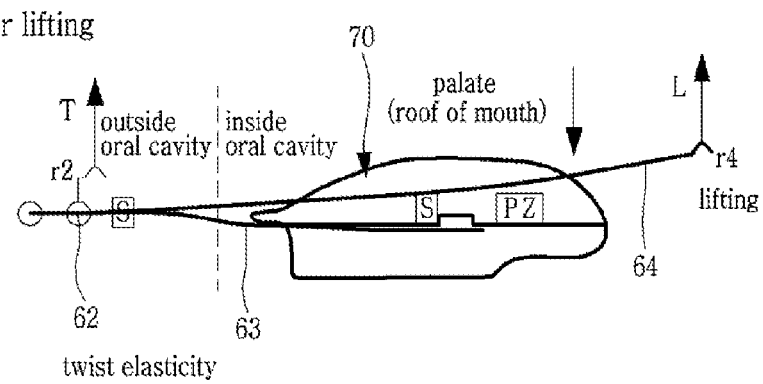

It is preferable that the mouthpiece 70 is brought into close contact with the palate in the oral cavity. To this end, as illustrated in FIG. 6, forward lifting of the mouthpiece 70 by upward traction of the respective rings r2 of the horizontal rod 62, and rearward lifting of the mouthpiece 70 by upward traction of the rings r4 of the outer peripheral portions extending from the horizontal rod 62 are simultaneously performed.

<Selection of Pad Position>

Figure 10:
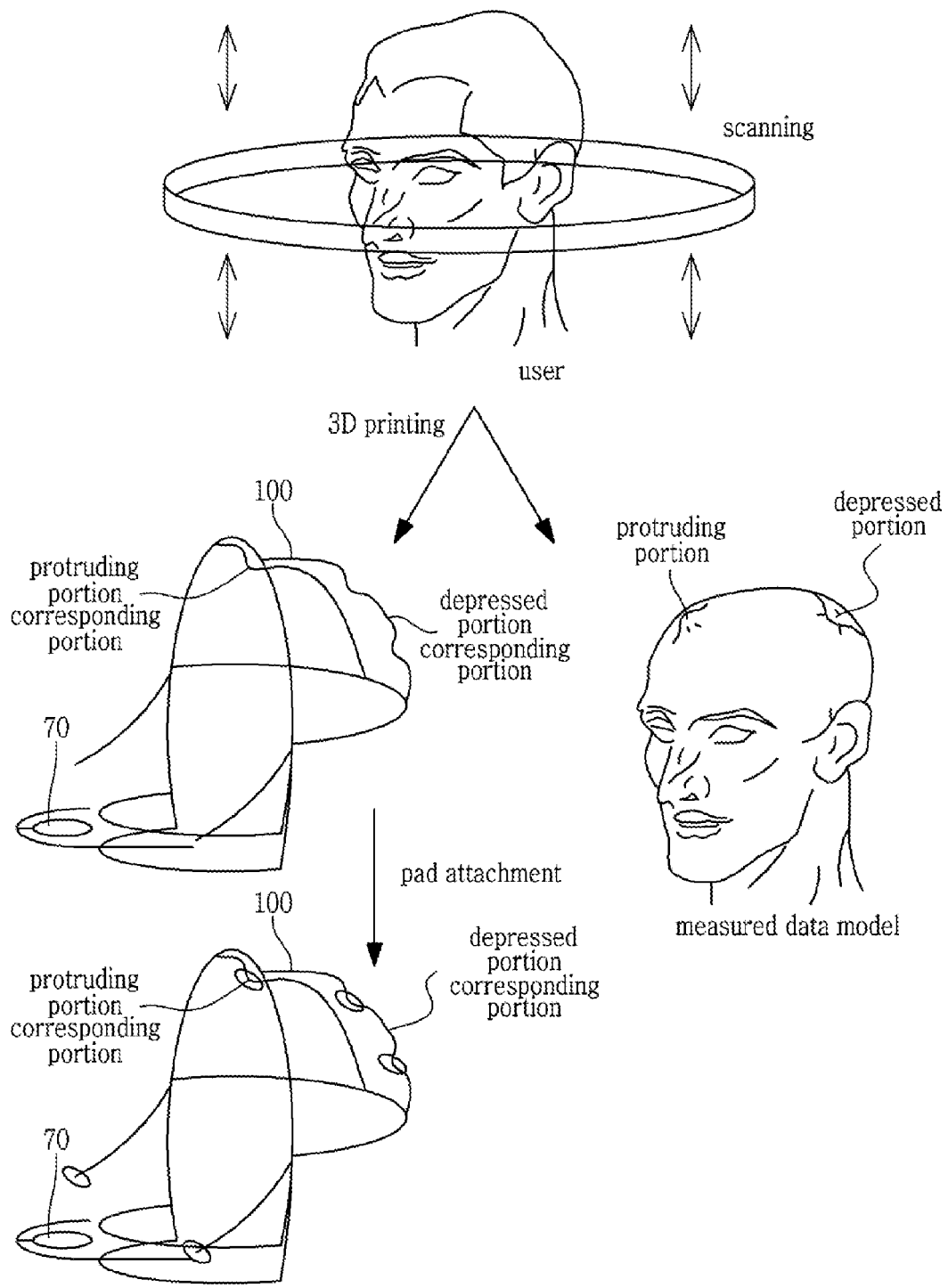
FIG. 10 is a view illustrating a configuration in which a measurement is made by scanning the user's head, and at least one of a mouthpiece and the headgear is custom-made by 3D printing from the measurement.
Figure 11:
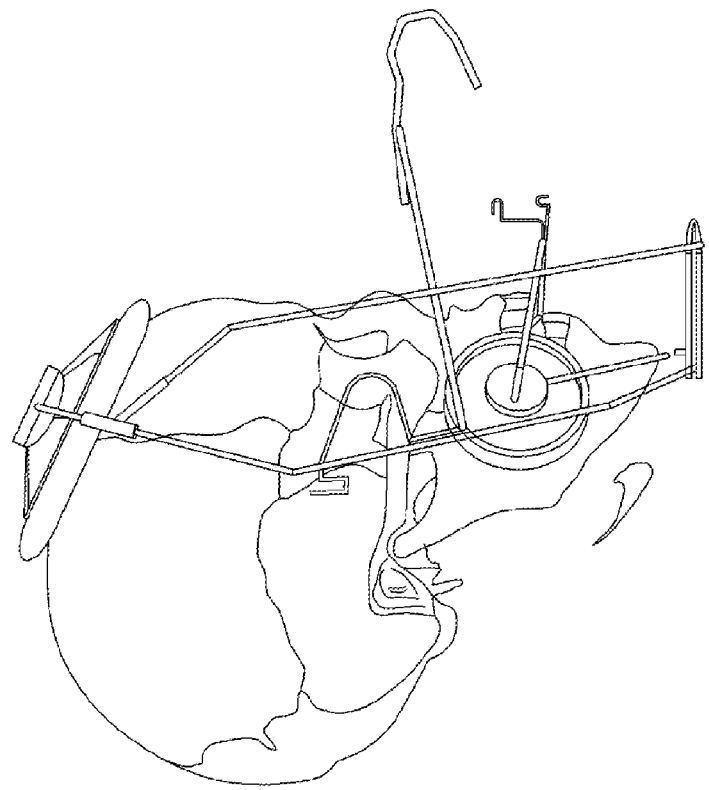
FIG. 11 is an illustration view of an example of a conventional art.
Figure 11:
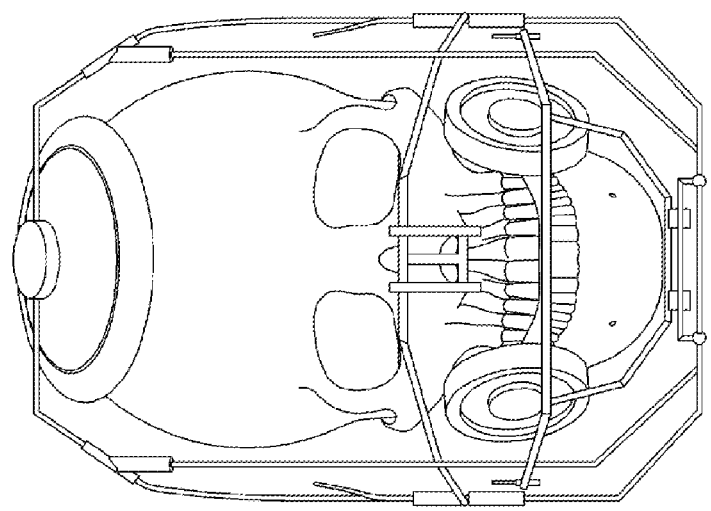

It is preferable that the shape or position of at least one of the mouthpiece 70 and the headgear 100 is personalized to the user so that paired forces are applied to a region necessary for symmetry formation of the head on the basis of the measured shape of the head of the user. Measurement of the head may be made, for example, by CT imaging (scanning), as illustrated in FIG. 10. Measurement results are read by an expert, and according to a result of reading, a front pressure point and a rear pressure point are selected in order to press in the direction such that an asymmetric portion of the head is removed. For example, a protruding portion of the head has to be pressed, and also the periphery of a depressed portion of the head has to be pressed.

The shape of the frames may be determined corresponding to the front pressure point and the rear pressure point selected in this way. That is, in the present invention, without the use of a ready-made frame as in a related art, the most optimal frame is individually custom-made according to the measured user's skull shape, thereby dramatically improving the accuracy of the pressing position and pressing force. Therefore, the headgear 100 can be properly worn to a correct position for pressing, the position of the headgear 100 after wearing can be maintained, soft tissue damage or hair loss due to friction can be prevented, and improvements in the depressed and protruding portions can be made accurately.

It is preferable that at least one of the mouthpiece 70 and the headgear 100 is formed by 3D printing on the basis of measured shape data. For example, as illustrated in FIG. 10, in the front frame 50 and the rear frames 10, 20, and 30, the shape of portions corresponding to the depressed and protruding portions of the user's head is appropriately deformed to form the headgear 100. The expert selects positions to which the front pads P4 and the rear pads P1 to P3 are attached on the basis of measured data, and attaches the pads to the headgear 100 custom-made as above.

Then, as illustrated in FIG. 10, on the basis of the measured shape of the head, a 3D measured data model may be made by, for example, 3D printing, and the expert may mark the front pressure point and the rear pressure point on the model with, for example, stickers. This provides an effect that even a non-expert can wear the headgear 100 by accurately matching the front pads and the rear pads to regions corresponding to the front and rear pressure points of the user's head, on the basis of the marked model.

<Electrical Device>

On the other hand, since the front pads P4 or the rear pads P1 to P3 are used in close contact with the facial skin, scalp, and hair, they are easy to be contaminated depending on the temperature or humidity and thus may cause sweat, acne, or the like. Therefore, temperature control (cooler and warmer), and ventilation control (blower and aspirator) are required. Provision of a light emitter that emits ultraviolet light for sterilization, far-infrared light for relaxing muscle skeletons, and various visible light, a sound device that produces sounds for pain relief, a low-frequency electric signal used for low-frequency treatment, and a vibrator that vibrate the skin may help prevent skin troubles or correct the skeleton by the headgear 100 or the mouthpiece 70. Therefore, it is preferable that a configuration for this is provided.

To this end, a power source 21 provided in at least one of the mouthpiece 70 and the headgear 100, and one or more function units 25 connected to the power source 21 to output a specific function may be provided. It is preferable that the function units 25 include at least one of (1) a light emitter that emits infrared light (including far-infrared light and near-infrared light), visible light (enhancing visual aesthetics and recreating treatment time), or ultraviolet light (sterilization), (2) a sound device that produces sounds, (3) a low-frequency electric signal that applies an electric signal to the muscle or skin, (4) a vibrator that outputs physical vibration, (5) a cooler or warmer that changes and controls temperature, and (6) a blower or aspirator that changes and controls ventilation.

The light emitter may be configured by, for example, an LED installed on the palate contact surface side of the mouthpiece 70 or on the skin contact surface side of the front pads P4 or the rear pads P1 to P3. The sound device may be configured by, for example, a speaker installed in the mouthpiece 70 or the headgear 100. The low-frequency electric signal may be configured by, for example, an electrode pad installed on the palate contact surface side of the mouthpiece 70 or on the skin contact surface side of the front pads P4 or the rear pads P1 to P3. The vibrator may be configured by, for example, an eccentric motor actuator installed in the mouthpiece 70 or the headgear 100. The cooler or the warmer may be configured by, for example, a semiconductor type Peltier effect element installed on the palate contact surface side of the mouthpiece 70 or the skin contact surface side of the front pads P4 or the rear pads P1 to P3. The blower or aspirator may be configured by, for example, a micro fan installed on the palate contact surface side of the mouthpiece 70 or the skin contact surface side of the front pads P4 or the rear pads P1 to P3, or by a vent hole connected through a flow path to an air compressor 22 provided in the mouthpiece 70 or the headgear 100.

The operation of the power source 21, the function units 25, or the compressor 22 may be performed, for example, by manually operating a switch (not illustrated).

<Power Generation and Storage Structure by Mouthpiece>

The power source 21 for the operation of the function units 25 may be an AC power source, or a primary or secondary battery or a solar cell (not illustrated). The function units may be operated by a renewable power source installed in the mouthpiece 70 and comprised of a generator (PZ) for generating electrical energy by relative motion between the maxilla and mandible, and a power storage means (not illustrated) for storing the generated electrical energy.

The generator (PZ) may be installed, for example, in the vicinity of the maxillary molars of the mouthpiece 70, and may be comprised of, for example, a stator fixed to the mouthpiece 70, and a mover installed to be able to reciprocate a predetermined distance without deviating from the stator. In principle, for example, a piezo effect element may be used, or an electromagnetic induction element that allows a permanent magnet to reciprocate in a micro-coil, or various other method may be used.

<Automatic Control by Sensor>

On the other hand, the operation of the power source 21, the function units 25, or the compressor 22 may be automated by a sensor unit S and a control unit 24.

To this end, at least one of the mouthpiece 70 and the headgear 100 may be further provided with one or more sensor units S provided to be connected to the power source 21, and the control unit 24 for controlling the function units 25 to be operated by comparing a detection value detected by the sensor units S with a predetermined reference value.

Here, it is preferable that
the sensor units include at least one of
(1) a temperature sensor,
(2) a humidity sensor,
(3) a skin resistance sensor,
(4) a tension sensor, and
(5) a distance sensor.

The temperature sensor may be configured by, for example, a wire-type thermometer or thermometer installed on the palate contact surface side of the mouthpiece 70 or on the skin contact surface side of the front pads P4 or the rear pads P1 to P3. The temperature sensor may be, for example, a sensor that detects a closed body temperature trapped between the scalp and a pad. The closed body temperature is a separate parameter from the outdoor temperature. For example, under strong sunlight conditions, even if the outdoor temperature is high, the closed body temperature of the scalp in contact with the pad may be lower than the outdoor temperature due to the UV blocking effect. Also for example, under cold weather conditions, even if the outdoor temperature is low, the closed body temperature of the scalp in contact with the pad may be higher than the outdoor temperature due to the cold prevention effect. The humidity sensor may be configured by, for example, a wire-type hygrometer installed on the palate contact surface side of the mouthpiece 70 or the skin contact surface side of the front pads P4 or the rear pads P1 to P3. The humidity sensor may be a sensor that detects a closed humidity trapped between the scalp and a pad. The closed humidity is also a separate parameter from the outdoor humidity. The skin resistance sensor may be configured by, for example, an electrode installed on the palate contact surface side of the mouthpiece 70 or the skin contact surface side of the front pads P4 or the rear pads P1 to P3. The skin resistance sensor is a sensor that detects the conductivity or resistance of the skin in contact with a pad. Skin resistance may depend, for example, on the amount of sweating. The tension sensor may be configured by, for example, a load meter installed on the palate contact surface side of the mouthpiece 70 or the skin contact surface side of the front pads P4 or the rear pads P1 to P3, a piezo effect element for detecting tension of the wires 63 protruding forward from the mouthpiece 70, or the horizontal bar 62 connected between the two wires 63, or a spring scale for detecting traction between the rings r1 and r2, the rings r3 and r4, and the rings r5 and r6. The distance sensor may be configured by, for example, a laser odometer for measuring a distance between division pieces of the mouthpiece 70, or a resistance odometer for converting a distance from a change in an electrical resistance value.

<Communication Function>

On the other hand, the headgear 100 is worn on the head has a constraint on weight, and thus there are cases in which it is preferable that complicated intelligent processing is configured to be processed by an external terminal (not illustrated).

To this end, it is preferable that at least one of the mouthpiece 70 and the headgear 100 is further provided with the communication unit 23, and the control unit 24 is configured to transmit a detection value detected by the sensor units S to a predetermined terminal (not illustrated) wirelessly through the communication unit 23.

According to this configuration, in accordance with detection values of temperature, humidity, skin resistance, tension, distance, and the like, operations such as light emission, sound production, low-frequency electric signal operation, vibration, cooling, warming, blowing, and suction are directly and automatically controlled by the control unit 24 in the mouthpiece 70 or the headgear 100, and the detection values are stored and accumulated in a terminal (not illustrated). Therefore, an alarm (including vision, hearing, vibration, and information) may be sent to a user or administrator, or statistical data of events to be solved for comfortable treatment, such as the number of troubles exceeding a reference value, may be presented. Alternatively, the detection values may be utilized as IoT medical big data by artificial intelligence.

On the other hand, furthermore, it is more preferable that the control unit 24 is configured to control the operation of at least one of the function units 25 in response to a command from the terminal (not illustrated) through the communication unit 23.

According to this, together with automatic control of the control unit 24 in the mouthpiece 70 or the headgear 100 itself, parameters such as temperature, humidity, electrical resistance, tension, and distance of the mouthpiece 70 or the headgear 100 may be returned to normal values by sending a command from an external terminal (not illustrated), and further, a reference value may be changed, and the function units 25 may be operated arbitrarily regardless of the reference value.

Although the embodiments of the present invention have been described in detail above with reference to with the accompanying drawings, those who are ordinarily skilled in the art will appreciate that various alternatives, modifications, and equivalents are possible, without changing the spirit or essential features of the present invention. Therefore, the embodiments of the present invention have been disclosed only for illustrative purposes and should not be construed as being restrictive.

INDUSTRIAL APPLICABILITY

The present invention can find application in the industry of headgear for fixing a mouthpiece.

The invention claimed is:

1. A headgear for fixing a mouthpiece, the headgear being worn on a user's head so as to adjustably fix the mouthpiece inserted in an oral cavity, and the headgear comprising:
   one or more front pads adapted to contact with one or more predetermined front pressure points, in a face region of the head;
   one or more rear pads adapted to contact with one or more predetermined rear pressure points so that a resultant force becomes a reaction force paired with a pressing force of the front pads, in a region from top to back of the head;
   a front frame configured to support the front pads;
   a rear frame configured to support the rear pads;
   a front horizontal bar configured to be connected to the front frame or the rear frame and adapted to be disposed in front of the lip region of the head, wherein the front horizontal bar has a double structure of an upper bar and a lower bar; and
   an adjustment part configured to be provided on a vertical rod installed between the upper bar and the lower bar, wherein the adjustment part is adapted to be disposed at a position in front of a lip region of the head to mount the mouthpiece,
   wherein the rear frame is adapted to be disposed above ear regions of the head, the front frame is adapted to be disposed in front of the ear region of the head, with one end thereof connected to the rear frame, and the other end thereof connected to the front pads, and the one or more predetermined front pressure points are predetermined portions of a maxilla on a face, and are positions that do not limit functions of eyes, a nose, and a mouth, and wherein the mouthpiece has a pair of wires protruding forward, front ends of the wires are connected to each other by a horizontal rod, and the horizontal rod extends to form an outer peripheral portion.

2. The headgear of claim 1, wherein the one or more predetermined front pressure points are positions of an outer surface of a buccinator between a zygomatic bone and a mandible.

3. The headgear of claim 2, wherein the front frame is configured to extend forward downward from the rear frame to pass through depressed portions between the ear regions and the zygomatic bone of the head and extend to below the zygomatic bone.

4. The headgear of claim 2, wherein in order to maximize an action force designed to be applied to the oral cavity by the mouthpiece, and to minimize a reaction force generated by the mouthpiece in response to the action force, the front and rear frames and the front and rear pads are formed such that the reaction force is transmitted to and canceled by at least one of the front and rear frames through the adjustment part.

5. The headgear of claim 1, wherein the front frame is configured to extend forward downward from the rear frame to pass through depressed portions between the ear regions and the zygomatic bone of the head and extend to below the zygomatic bone.

6. The headgear of claim 1, wherein in order to maximize an action force designed to be applied to the oral cavity by the mouthpiece, and to minimize a reaction force generated by the mouthpiece in response to the action force, the front and rear frames and the front and rear pads are formed such that the reaction force is transmitted to and canceled by at least one of the front and rear frames through the adjustment part.

* * * * *